United States Patent
Tanaka et al.

(10) Patent No.: US 6,509,178 B1
(45) Date of Patent: Jan. 21, 2003

(54) PROCESS FOR PREPARING DOCOSAHEXAENOIC ACID AND DOCOSAPENTAENOIC ACID WITH ULKENIA

(75) Inventors: Satohiro Tanaka, Shiso-gun (JP); Toshiaki Yaguchi, Mishima-gun (JP); Sakayu Shimizu, Kyoto (JP); Tsutomu Sogo, Kobe (JP); Shigeaki Fujikawa, Takatsuki (JP)

(73) Assignees: Suntory Ltd., Osaka (JP); Nagase & Co., Ltd., Osaka (JP); Nagase Chemtex Corporation, Osaka (JP)

( * ) Notice: Subject to any disclaimer, the term of this patent is extended or adjusted under 35 U.S.C. 154(b) by 0 days.

(21) Appl. No.: 09/230,212

(22) PCT Filed: Jun. 6, 1997

(86) PCT No.: PCT/JP97/01946

§ 371 (c)(1),
(2), (4) Date: May 3, 1999

(87) PCT Pub. No.: WO98/03671

PCT Pub. Date: Jan. 29, 1998

(30) Foreign Application Priority Data

Jul. 23, 1996 (JP) ............................................. 8-193516

(51) Int. Cl.$^7$ .................................................. C12P 7/64
(52) U.S. Cl. ...................... 435/134; 435/135; 435/170; 435/257.1; 435/254.1
(58) Field of Search ................................. 435/134, 135, 435/170, 257.1, 254.1

(56) References Cited

U.S. PATENT DOCUMENTS 5,340,742 A    8/1994    Barclay
5,397,591 A    3/1995    Kyle et al.

FOREIGN PATENT DOCUMENTS

JP           09030962 A      2/1997
WO     WPI 97-161410    2/1997

OTHER PUBLICATIONS

Shimada, et al., J. Ferment. Bioeng. (1996), 81(4), 299–303.*
Yadwad et al., Biotechnol. Bioeng. (1991), 38(8), 956–9.*
Gaertner, Alwin, Veroff. Inst. Meeresforsch, Bremerh., *Revision of the Thraustochytriaceae (Lower Fungi) I. Ulkenia nov. gen., with Description of Three New Species*, 16, 1977, pp. 139–157.
Moss, Stephen, The Biology of Fee–living Heterotrophic Flagellates, *Thraustochytrids and Other Zoosporic Marine Fungi*, Special Volume No. 45, 1991, pp. 415–25.
Moss, S.T., The Biology of Marine Fungi, *Biology and Phylogeny of the Labyrinthulales and Thraustochytriales*, 1986, pp. 105–129.
Singh, A. et al., World Journal of Microbiology & Biotechnology, *Docosahexaenoic Acid (DHA) Production by Thraustochytrium sp. ATCC 20892*, vol. 12, 1996, pp. 76–81.
Akoh, C., Inform, *Structured Lipids–Enzymatic Approach*, vol. 6, No. 9, Sep. 1995, pp. 1055–1061.

* cited by examiner

*Primary Examiner*—Irene Marx
(74) *Attorney, Agent, or Firm*—Howrey Simon Arnold & White

(57) ABSTRACT

A process for preparing lipids which contain docosahexaenoic acid (DHA) and/or docosapentaenoic acid (DPA) is disclosed. The process includes the steps of cultivating in a medium a microorganism which belongs to the genus Ulkenia having the ability to produce DHA and/or DPA and recovering the lipids from the culture. The process may further include the step of separating DHA and/or DPA from the lipids.

4 Claims, 1 Drawing Sheet

PROCESS FOR PREPARING DOCOSAHEXAENOIC ACID AND DOCOSAPENTAENOIC ACID WITH ULKENIA

TECHNICAL FIELD

The present invention relates to a process for preparing lipids containing docosahexaenoic acid (hereinafter, also referred to as "DHA") and/or docosapentaenoic acid (hereinafter, also referred to as "DPA") by cultivating a microorganism, as well as a process for preparing DHA and/or DPA from the lipids. The present invention also relates to a microorganism belonging to the genus Ulkenia having the ability to produce the lipids.

BACKGROUND ART

DHA is contained in oil from fish belonging to the group of blue fish. Particularly, DHA is contained in the oil from sardines or tuna, in which DHA is contained in an amount of around 20%.

Recently, due to the discovery of fish material containing a high concentration of DHA such as the orbital fat of tuna, or due to the progress in technology for producing highly purified fatty acids, intensive efforts have been made to elucidate the physiological functions of DHA, and to investigate its practical use. It has become apparent that the physiological functions of DHA include an effect of lowering cholesterol, an anticoagulant effect and a carcinostatic effect. In relation to the metabolic system of brain, it has also become apparent that DHA is effective in improving memory and learning, preventing senile dementia, and treating Alzheimer's disease. In addition, it has been proved that DHA is an essential fatty acid for the growth of fry. For the reasons mentioned above, DHA is used in various foods, feedstuffs and baits.

DPA is also known to be contained in fish oil, although the content is extremely low. Most of the physiological functions of DPA are still unknown. The only function known for DPA is its usefulness as a carrier for transporting pharmaceutical agents into brain [Japanese Patent Publication (Kokai) No. 61-204136 (1986)]. It is expected, however, that DPA may play a physiological role in the animal body, since it is known that DPA increases in compensation for a lack of DHA in an animal body [Homayoun et al., J. Neurochem., 51:45 (1988); Hamm et al., Biochem. J., 245:907 (1987); and Rebhung et al., Biosci. Biotech. Biochem., 58:314 (1994)].

If one intends to obtain DHA and/or DPA from fish oil, several disadvantages exist, for example; the low content of the desired fatty acids, the inability to maintain a stable source of fish oil due to the migration of fish, or the offensive odor inherent in fish oil. In addition, it is difficult to obtain lipids with reliable quality, since fish oil additionally contains unsaturated fatty acids such as arachidonic acid (ARA) and eicosapentaenoic acid (EPA), which makes the lipids susceptible to oxidization.

Besides fish oil, lipids accumulated in cultured cells of a microorganism having an ability to produce DHA and/or DPA is considered as a source of DHA and/or DPA. For example, the following microorganisms are known to produce DHA and/or DPA: *Vibrio marinus* ATCC 15381, a bacterium isolated from the deep sea; Vibrio bacteria isolated from an intestines of a deep-sea fish; flagellate fungi such as *Thraustochytrium aureum* ATCC 34304, Thraustochytrium sp. ATCC 28211, ATCC 20890 and ATCC 20891, Schizochytrium sp. ATCC 20888 and ATCC 20889 (U.S. Pat. No. 5,340,742), Thraustochytrium SR21 strain (Nippon Nogei Kagaku Kaishi, vol.69, extra edition. Jul. 5, 1995), and Japonochytrium sp. ATCC 28207 [Japanese Patent Publication (Kokai) No. 1-199588 (1989)]; micro-algae such as *Cyclotella cryptica, Crypthecodinium cohnii* [Japanese Patent Publication (Kohyo) No. 5-503425 (1993)], and Emiliania sp. [Japanese Patent Publication (Kokai) No. 5-308978 (1993)].

In using any of the above-mentioned microorganisms, however, several problems exist, for example, a low yield of DHA and/or DPA, a requirement of a prolonged culture period for obtaining a sufficient amount of DHA and/or DPA, or a requirement of a specific medium or culture condition for production. When an alga such as Emiliania sp. is utilized for the production, a high yield of DHA may be accomplished, although there may exist a disadvantage that the culture steps are complicated due to the requirement of light for cultivation. Consequently, such a process is not suitable for industrial production.

Thus, the present invention described herein makes possible the advantage of providing a process which can produce DHA and/or DPA as well as lipids containing DHA and/or DPA using an inexpensive and conventional medium and simple steps for production, in a short period and in a high yield.

The present invention provides a process for preparing lipids containing DRA and/or DPA comprising cultivating in a medium a microorganism belonging to the genus Ulkenia having the ability to produce DHA and/or DPA, and recovering the lipids from the culture.

The present invention also provides a process for preparing DHA and/or DPA comprising cultivating in a medium a microorganism belonging to the genus Ulkenia having the ability to produce DHA and/or DPA, recovering the lipids from the culture, and separating the DHA and/or DPA from the lipids.

DISCLOSURE OF THE INVENTION

A process for preparing lipids containing docosahexaenoic acid and docosapentaenoic acid according to the present invention comprises cultivating in a medium a microorganism belonging to the genus Ulkenia having the ability to produce lipids containing docosahexaenoic acid and docosapentaenoic acid, and recovering said lipids from a culture.

A process for preparing docosahexaenoic acid according to the present invention comprises cultivating in a medium a microorganism belonging to the genus Ulkenia having the ability to produce lipids containing docosahexaenoic acid, recovering said lipids from the culture, and separating said docosahexaenoic acid from said lipids.

A process for preparing docosapentaenoic acid according to the present invention comprises cultivating in a medium a microorganism belonging to the genus Ulkenia having the ability to produce lipids containing docosapentaenoic acid, recovering said lipids from the culture, and separating said docosapentaenoic acid from said lipids.

The present invention provides cells of a microorganism belonging to the genus Ulkenia containing lipids containing docosahexaenoic acid and/or docosapentaenoic acid.

The present invention provides an Ulkenia sp. SAM2179 strain having the ability to produce lipids containing docosahexaenoic acid and docosapentaenoic acid.

The present invention provides a nutrient-supplementing food, a formula suitable for feeding infants, a formula suitable for feeding immature infants, a baby food, a food for expectant or nursing mothers, a geriatric food, an enteral agent for promoting nutrition, a feed for animals, an additive for a feed for animals, and a bait for microorganisms for baits containing the lipids obtained by any one of the above-mentioned processes.

A process for preparing structured lipids containing docosahexaenoic acid and docosapentaenoic acid of the present invention comprises cultivating in a medium a microorganism belonging to the genus Ulkenia having the ability to produce lipids containing docosahexaenoic acid and docosapentaenoic acid, recovering said lipids from a culture, and treating said lipids with fungal lipase to convert fatty acids at positions 1 and 3 into medium chain (C:8–12, see "SEIKAGAKUJITEN" (second edition) pp. 834, TOKYO KAGAKUDOJIN (1990)) fatty acids.

BEST MODE FOR CARRYING OUT THE INVENTION

Figure 1:
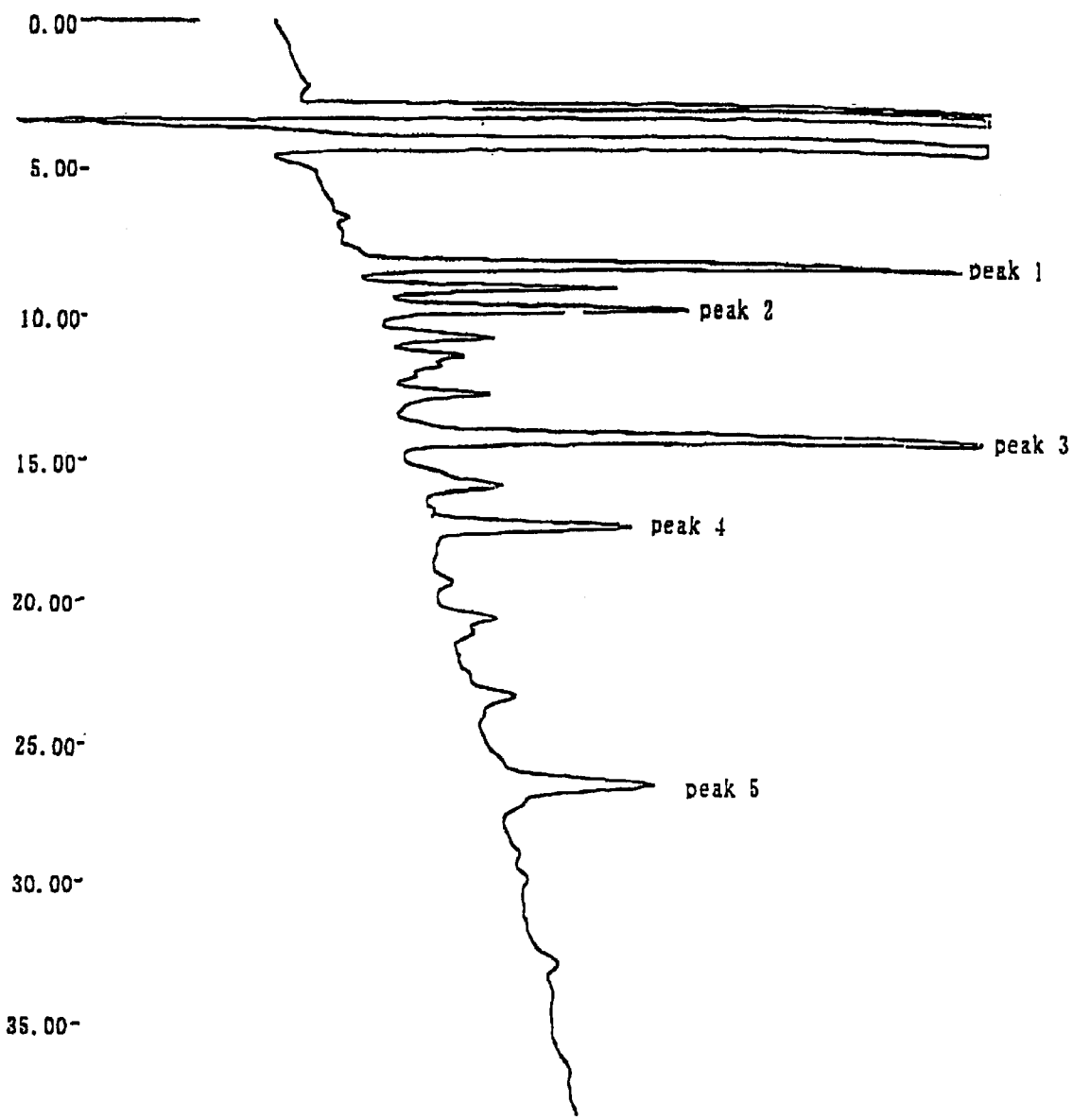
FIG. 1 is a liquid chromatogram of triacylglycerols in neutral lipid obtained by the present invention.

The present invention is described in more detail below. As used herein, the term "docosahexaenoic acid" or "DHA" refers to the (n-3) series of docosahexaenoic acid. As used herein, the term "docosapentaenoic acid" or "DPA" refers to the (n-3) series and/or (n-6) series of docosapentaenoic acid. The terms "fats", "lipids" and "oil" are used herein in the same meaning.

Any microorganisms belonging to the genus Ulkenia can be used in the process of the present invention, as long as they have the ability to produce DHA and/or DPA. For example, Ulkenia sp. SAM 2180 and SAM 2179 strains isolated from sea water by the present inventors can be used. Among these strains, the SAM 2179 strains produces both DHA and DPA to a greater degree. This strain was deposited with the National Institute of Bioscience and Human-Technology, Agency of Industrial Science and Technology (address: 1-3, Higashi 1 chome Tsukuba-shi Ibaraki-ken 305, JAPAN), on Jul. 23, 1996 and assigned an accession number FERM BP-5601.

The mycological characteristics of the Ulkenia sp. SAM 2179 and SAM 2180 strains are as follows. When these microorganisms were cultured in a KMV liquid medium (Fuller. M. and A. Jaworski eds.; Zoosporic Fungi in Teaching & Research VII +303pp., 1987. Southeastern Publishing Corporation, Athens) at 20° C. in the dark, globose or oval cells were observed, and biflagellate zoospores were also observed. However, a network of ectoplasm filaments was not observed. Accordingly, these microorganisms were classified into fungi belonging to Thraustochytriales with reference to "Icons of the Japanese Water Mould with Precise Explanation" by Yosio Kobayasi and Kazuko Konno (published privately by the authors at their own expense, p.169, 1986). Furthermore, these microorganisms formed rhizoids, lacked apophyses, and formed amoeba-like cells in the KMV liquid medium. Therefore, they were identified as fungi belonging to the genus Ulkenia, and the two isolates were designated as Ulkenia sp. SAM 2179 and SAM 2180, respectively.

The microorganism belonging to the genus Ulkenia used in the process of the present invention is not limited to a wild-type strain, but may also include a mutant or a recombinant strain. Thus, the use of a mutant or a recombinant strain designed to efficiently produce DHA and/or DPA falls within the scope of the present invention. Such mutants or recombinant strains include microorganisms designed to contain a higher percentage of DHA and/or DPA in lipids, a higher total amount of the lipids, or both, in comparison with the percentage or the amount produced by the original wild-type strain, utilizing the same substrates. The wild-type strain according to the present invention contains at least 25% DHA and/or 5% DPA, preferably 40–48% DRA and/or 8–13% DPA in the lipids. Furthermore, the wild-type strain according to the present invention contains at least 3 g of DHA and/or 0.5 g of DPA, preferably 5 g of DHA and/or 1 g of DPA per liter of medium. In addition, microorganisms designed to produce a comparable amount of DRA and/or DPA with the corresponding wild-type strain, efficiently utilizing substrates with a superior cost performance, are also contemplated.

The microorganisms according to the present invention are cultured by inoculating a liquid or solid medium with a pre-culture of the microorganisms. The medium may or may not contain natural or artificial sea water.

Any conventionally used carbon sources including, for example, but not limited to, carbohydrates such as glucose, fructose, xylose, saccharose, maltose, soluble starch, fucose, glucosamine and dextran, as well as oleic acid, fats such as soybean, oil, glutamic acid, molasses, glycerol, mannitol, and sodium acetate may be used as a carbon source to be added to the medium.

Natural nitrogen sources such as peptone, yeast extract, malt extract, meat extract, casamino acid and corn steep liquor, soybean cake, organic nitrogen sources such as sodium glutamate and urea, and inorganic nitrogen sources such as ammonium acetate, ammonium sulfate, ammonium chloride and ammonium nitrate may be used as a nitrogen source.

Furthermore, phosphates such as potassium phosphate and potassium dihydrogen phosphate, inorganic salts such as ammonium sulfate, sodium sulfate, magnesium sulfate, iron sulfate, copper sulfate, magnesium chloride and calcium chloride and vitamins may be added as micronutrients, if required.

The amount of these components in the medium is not specifically defined, as long as the concentrations of the components do not have a harmful effect on the growth of microorganisms. In general, the carbon sources may be added at a concentration of 20 to 180 g per liter of medium, and the nitrogen sources may be added at a concentration of 0.6 to 6 g per liter of medium. Preferably, the amount of the nitrogen source is increased in correspondence with the increase in the amount of the carbon source.

After preparing the medium, its pH is adjusted to the range between 3.0 and 8.0, preferably between 3.5 and 5.0, more preferably between 3.5 and 4.5, using a suitable acid or base, and then the medium is sterilized by autoclaving or the like. Cultivation of a microorganism is usually carried out for 2 to 7 days, preferably for 2 to 5 days, at 10 to 35° C., preferably at 17 to 30° C., either with aeration-agitation, with shaking, or in a stationary culture.

Furthermore, precursors of DHA and/or DPA may be added to the medium in order to accelerate the production of DHA and/or DPA. For example, hydrocarbons such as tetradecane, hexadecane and octadecane, fatty acids such as oleic acid, linoleic acid and α-linolenic acid, or salts (e.g. sodium or potassium salts) or esters thereof are used as precursors. Furthermore, fats containing these fatty acids as a constituent (e.g. olive oil, soybean oil, cottonseed oil or palm oil) may be added. These components may be used alone or in combination with one another.

Carbon sources, nitrogen sources, precursors or the like may be added to the medium before or during the cultivation. The addition of these components may be carried out once, repeatedly or continuously.

In order to recover lipids containing DHA and/or DPA in a suitable yield for practical use, it is preferable to use a liquid medium and to cultivate with aeration-agitation. A conventional agitation-fermentor or a bubble column fermentor may be used.

By cultivating as described above, lipids containing DRA and/or DPA is produced and accumulated in cells. When a liquid medium is used, lipids which contains DHA and/or DPA may be recovered from a culture, or a sterilized culture, during the cultivation period, from a culture, or a sterilized culture, at the end of cultivation, or from cultured cells, or dried cells, collected from any one of the above-mentioned cultures. As used herein, the term "culture" includes cultured cells, dried cultured cells and processed cultured cells as well as culture broth containing cells and culture supernatant.

DHA and/or DPA may be isolated from lipids containing DHA and/or DPA recovered from cultured cells, as follows. After cultivation, cells are collected from the culture by conventional solid/liquid separation means such as centrifugation and filtration. The cells are extensively washed with water, and preferably, they are then dried. The drying of the cells may be carried out by freeze-drying, air-drying or the like. The dried cells are then destroyed, for example, by means of dyno-mill or ultrasonication, and lipids are extracted from the cells with an organic solvent, preferably under nitrogen stream. Organic solvent such as ether, hexane, methanol, ethanol, chloroform, dichloromethane or petroleum ether may be used. Alternate extraction with methanol and petroleum ether or extraction with a mixed solvent system of chloroform/methanol/water may also used. A high concentration of lipids containing DHA and/or DPA is obtained by evaporating the organic solvent from the extract under a reduced pressure.

Alternatively, the extraction may be carried out with wet cells. In this case, a solvent compatible with water such as methanol and ethanol, or a mixed solvent compatible with water consisting of the alcohol(s) and water and/or other solvents may be used. The other procedures are as described above.

The amount of DHA in the lipids obtained as described above is at least 3 g per liter of culture, preferably 5 g per liter of culture. The amount of DPA in the lipids is at least 0.7 g per liter of culture, preferably 1.0 g per liter of culture.

In the lipids obtained as described above, DHA and/or DPA are present in the form of a neutral lipids (e.g. triacylglycerol) or a polar lipids (e.g. phosphatidylcholine phosphatidylethanolamine or phosphatidylinositol). Purification of triacylglycerols containing DHA and/or DPA from lipids containing DHA and/or DPA recovered from a culture is carried out by using a conventional method such as cooling-separation or column chromatography.

Typically, the content of neutral lipids in the lipids of the present invention is very high (more than 90% of total lipids). The representative composition of fatty acids in the neutral lipids is as follows. Palmitic acid: 30–38%; (n-3) DHA: 40–48%; (n-6) DPA: 8–13%; (n-3) EPA: 0–1%; ARA: 0–0.6%; other fatty acids: 10–20%.

The neutral lipids from the lipids of the present invention contain at least 85% triacylglycerols, preferably at least 90% triacylglycerols. The amount of diacylglycerols or monoacylglycerols in the neutral lipids is very low. Free sterol and/or sterol ester also is contained in an amount of 1–3%. Typically, the following molecular species are found in the triacylglycerols: 16:0–16:0–22:5, 16:0–16:0–22:6, 16:0–22:5–22:6, 16:0–22:6–22:6, 22:5–22:6–22:6, and 22:6–22:6–22:6, wherein, for example, "16:0" means a fatty acid having "16" carbon atoms and no ("0") double bonds. It is interesting that triacylglycerols consisting of only polyunsaturated fatty acids exist in the lipids of the present invention.

Separation of DHA and/or DPA from lipids containing DHA and/or DPA may be carried out by hydrolyzing the lipids, and then concentrating and separating the resulting mixed fatty acids or mixed fatty acid esters prepared therefrom, by using a conventional method such as urea-addition, cooling-separation or column chromatography.

The DHA and/or DPA as well as the lipids containing DHA and/or DPA obtained as described above can be added to various foods, feedstuffs or baits to counter a deficiency of DHA and/or DPA. Examples of such foods include, for example, nutrient-supplementing foods, formula suitable for feeding infants or immature infants, health foods, functional foods (such as an enteral agent for promoting nutrition), baby foods, foods for expectant or nursing mothers and geriatric foods. Feedstuffs include feed for domestic animals such as pigs and cows, feed for domestic fowl such as chickens, pet foods for dogs, cats and the like, and feed for fish breeding. Baits include, for example, those for microorganisms (so-called zooplanktons) which are given as a bait for culturing fish and shellfish.

Particularly, for feedstuffs and baits, it is advantageous and economical to use a culture of a microorganism of the present invention, cells collected from the culture, or a residue of the cells after the recovery of the lipids. For example, cells of microorganisms which produce DHA and/or DPA may be directly used to feed fry (the young of fishes), instead of indirectly feeding them through zooplanktons and the like. These materials may be used after drying or sterilizing, if necessary.

The lipids of the present invention may be used for producing poultry eggs enriched with DHA and/or DPA, which are obtained by feeding poultries for ovum-collection (preferably chickens) with feed containing the lipids of the present invention. Egg yolk oil enriched with DHA and/or DPA may also be produced by extracting oil from such poultry eggs or egg yolk therefrom using a conventional method. Formula suitable for feeding infants and immature infants, baby food, food for expectant and nursing mothers containing such egg yolk oil are also contemplated.

Efforts have been made for long to make the composition of powdered milk for babies similar to that of human milk. In particular, it is important to make the composition of the main ingredients of human milk (i.e., protein, fat, and sugar) in powdered milk similar to that of human milk. Regarding lipids, it has been a problem that the conventional powdered milk is deficient in polyunsaturated fatty acids, which are inherently contained in human milk. Several reports on the composition of unsaturated fatty acids in human milk have been published (for polyunsaturated fatty acids in American, European, and African mothers milk, see INFORM, 6(8) :940–946 (1995); for polyunsaturated fatty acids in Japanese mothers' milk, see JJPEN, 13(9):765–772 (1991)).

Recently, it was demonstrated that ARA and DHA, both of which are contained in human milk, are effective in the growth of babies ("Advances in Polyunsaturated Fatty Acid Research", Elsevier Science Publishers, pp.261–264 (1993)). The importance of ARA and DRA in the increase of height and the development of brain was also reported (Proc. Natl. Acad. Sci. USA, 90:1073–1077 (1993); Lancet, 344:1319–1322 (1994)).

Therefore, there exists an increasing interest in adding ARA and DHA to modified milk. Modified milk containing fish oil as a source for DHA are now on the market. Fish oil also contains EPA, which is scarcely present in human milk, and which has been reported to render an adverse effect on growth of immature infants ("Advances in Polyunsaturated Fatty Acid Research", Elsevier Science Publishers, pp.261–264 (1993)). The lipids of the present invention are suitable as an additive to modified milk, since the content of EPA is extremely low. The lipids of the present invention can be added to baby food as well.

The lipids of the present invention may be added to food, such as nutrient-supplementing food, geriatric food, or health food, for the supply of DHA and/or DPA or for the maintenance of health. The food composition may be in the form of solid or liquid foods, or foods containing oils. The content of lipids in the food is preferably between 0.001 to 50% by weight, depending on the nature of the food to which the lipids are added.

Examples of foods containing oils include natural foods inherently containing oils (such as meat, fish or nut), food to which the lipids are added upon cooking (such as soup), food for which the lipids are used as heating medium (such as doughnuts), fat food (such as butter), processed food into which the lipids are added upon processing (such as cookies), or food to which the lipids are sprayed or applied upon completion of processing (such as hard biscuits). The lipids (or separated DHA and/or DPA) of the present invention may also be added to agricultural food, fermentation food, livestock food, sea food, or drink, which does not contain fats.

Alternatively, the lipids of the present invention may also be added to a functional food which exhibits the physiological activity of DHA and/or DPA for the recovery of a lowered function of body or for the prevention of lowering it. The functional food of the present invention may be in a form of a medical formulation or in a processed form (such as an enteral agent for promoting nutrition, powder, granule, troche, internal solution, suspension, emulsion, syrup and the like) in which the lipids of the present invention are combined with protein, saccharide, lipid, trace elements, vitamin, emulsifying agent, or perfume.

Furthermore, the lipids of the present invention may be used as an additive for a cosmetic or a wash, or a starting material for producing a derivative thereof to be used as a medicament.

Hereinafter, the present invention will be specifically described by way of examples. However, the invention is not limited to the examples.

EXAMPLE 1

Production of Lipids Using Microorganisms Belonging to the Genus Ulkenia (1)

The Ulkenia sp. SAM 2180 and SAM 2179 strains were cultivated in a 5 liter (L) volume fermentor (jar fermentor) containing 3 L of medium having the following composition under the following culture conditions.

(1) Medium composition
1) Glucose (g/L): 60
2) Potassium phosphate (g/L): 3
3) Ammonium sulfate (g/L): 2
4) Corn steep liquor (g/L): 0.7
5) 50% Artificial sea water (L): 1
6) pH: 4.0

(2) Culture conditions
1) Culturing temperature (°C.): 28
2) Aeration amount (VVM): 0.5
3) Agitation rate (rpm): 300
4) pH Adjustment: maintained at pH 4 with 10% (w/v) sodium hydroxide and 1 M sulfuric acid After cultivation, cells were collected by centrifugation and freeze-dried, then the amount (by weight) of cells per liter of medium was measured. Destruction of the cells and extraction of the lipids were then carried out by adding a mixture of chloroform/methanol (2:1, v/v) to the dried cells at a ratio of 100 volumes per weight of the cells and homogenizing the mixture in the presence of glass beads. After washing the extract according to the Folch method, the solvent was evaporated to obtain purified lipids, and the weight of the lipids was then measured.

In order to estimate the fatty acid composition of the resulting purified lipids, fatty acid methyl esters were prepared by dissolving a portion of the lipids in a mixed solution of an equal amount of methanol solution containing 10% HCl and dichloromethane, and heat-treating the mixture at 60° C. for 2 hours. The esters were then subjected to gas chromatography to analyze the fatty acid composition. The separation conditions for the gas liquid chromatography were as follows.

(3) Separation conditions
1) Column: capillary column TC-70 (GL Science Co., LTD.), inner diameter 0.25 mm×length 30 m
2) Flow rate: 0.8 ml/min, 100 kPa (column head pressure)
3) Carrier gas: nitrogen gas
4) Column temperature: rising mode, 170–220° C. (4° C./min.)
5) Detection: FID The results are shown in the following Tables 1 and 2.

TABLE 1

| Strain | Cultivation time (days) | Dry cell weight (g)*1 | Total amount of lipids (g)*1 | Percent of lipids content (wt %)*2 | Amount of DHA (g)*1 | Amount of DPA (g)*1 |
|---|---|---|---|---|---|---|
| SAM2180 | 3 | 23.2 | 14.1 | 61 | 4.0 | 0.9 |
| SAM2179 | 3 | 19.5 | 11.9 | 61 | 5.5 | 1.3 |

*1) Weight per liter of medium
*2) Percentage versus dried cells

TABLE 2

| Strain | 14:0 | 15:0 | 16:0 | 17:0 | 18:0 | 20:4 (AA) | 20:5 (EPA) | 22:5 (DPA) | 22:6 (DHA) |
|---|---|---|---|---|---|---|---|---|---|
| SAM2180 | 2.7 | 2.4 | 55.0 | 1.0 | 1.4 | — | 0.2 | 6.7 | 28.7 |
| SAM2179 | 2.4 | 0.9 | 37.2 | 0.3 | 0.8 | 0.4 | 0.6 | 10.6 | 46.2 |

EXAMPLE 2

Production of Lipids Using Microorganism Belonging to the Genus Ulkenia (2)

The Ulkenia sp. SAM 2179 strain was cultivated in a 5 L volume fermentor (jar fermentor) containing 3 L of medium having the following composition under the following culture conditions.

(1) Medium composition
1) Glucose (g/L): 60
2) Potassium phosphate (g/L): 3
3) Ammonium sulfate (g/L): 2
4) Magnesium chloride (g/L): 1.3
5) Sodium sulfate (g/L): 1
6) Calcium chloride (g/L): 0.3
7) Corn steep liquor (g/L): 0.7
8) pH: 4.0

(2) Culture conditions
1) Culturing temperature (°C.): 28
2) Aeration amount (VVM): 0.5
3) Agitation rate (rpm): 300
4) pH Adjustment: maintained at pH 4 with 10% (w/v) sodium hydroxide and 1 M sulfuric acid After cultivation, cells were collected by centrifugation and freeze-dried, then the amount (by weight) of cells per liter of medium was measured. Destruction of the cells and extraction of the lipids were then carried out by adding a mixture of chloroform/methanol (2:1, v/v) to the dried cells at a ratio of 100 volumes per weight of the cells and homogenizing the mixture in the presence of glass beads. After washing the extract according to the Folch method, the solvent was evaporated to obtain purified lipids, and the weight of the lipids was then measured.

In order to estimate the fatty acid composition of the resulting purified lipids, fatty acid methyl esters were prepared by dissolving a portion of the lipids in a mixed solution of an equal amount of methanol solution containing 10% HCl and dichloromethane, and heat-treating the mixture at 60° C. for 2 hours. The esters were then subjected to gas chromatography to analyze the fatty acid composition. The separation conditions for the gas liquid chromatography were as described in Example 1.

The results are shown in the following Tables 3 and 4.

TABLE 3

| Strain | Cultivation time (days) | Dry cell weight (g)*1 | Total amount of lipids (g)*1 | Percent of lipids content (wt %)*2 | Amount of DHA (g)*1 | Amount of DPA (g)*1 |
|---|---|---|---|---|---|---|
| SAM2179 | 3 | 21.5 | 12.0 | 56 | 5.5 | 1.5 |

*1) Weight per liter of medium
*2) Percentage versus dried cells

TABLE 4

| Strain | 14:0 | 15:0 | 16:0 | 17:0 | 18:0 | 20:4 (AA) | 20:5 (EPA) | 22:5 (DPA) | 22:6 (DHA) |
|---|---|---|---|---|---|---|---|---|---|
| SAM2179 | 2.0 | 1.5 | 34.3 | 0.5 | 0.9 | 0.7 | 0.7 | 12.4 | 45.8 |

EXAMPLE 3

Analysis of Lipids from Ulkenia sp. SAM 2179

Neutral lipids and polar lipids were separated from the lipids obtained in Example 1 by conventional liquid-liquid partition technique using hexan and 90% methanol. 0.92 g of neutral lipids and 0.05 g of polar lipids were obtained from 1 g of the lipids, respectively. The resulting neutral lipids and polar lipids were analyzed using thin-layer chromatography. Color development was accomplished by using sulfuric acid, then the identity of the resulting spots were confirmed by comparing their Rf values with those of standard lipids.

More than 90% of the neutral lipids were triacylglycerols. The polar lipids consist of phosphatidylcholine (60–80%), phosphatidylethanolamine (5–20%) and phosphatidylinositol (2–8%).

The triacylglycerols in the neutral lipids were further analyzed by separating molecular species on liquid chromatography (column: ODS column; mobile phase: acetone/acetonitrile (3:2); detection: differential refractometer) (see FIG. 1). The resulting peaks were isolated and, after hydrolysis, converted to methylesters. The fatty acid residues were determined by using gas liquid chromatography.

The five main peaks were identified as shown in Table 5. Triacylglycerols were composed of 12.8% 1,2,3-tri-docosahexaenoyl-triacylglycerol and 8.0% 1-docosapentaenoyl-2,3-di-docosahexaenoyl-triacylglycerol. About 20% of the total triacylglycerols were composed of tri-polyunsaturated fatty acids.

TABLE 5

| Peak | Molecular species | Ratio (%) |
|---|---|---|
| 1 | 22:6-22:6-22:6 | 12.8 |
| 2 | 22:5-22:6-22:6 | 8.0 |
| 3 | 16:0-22:6-22:6 | 18.3 |
| 4 | 16:0-22:5-22:6 | 8.1 |
| 5 | 16:0-16:0-22:6 | 10.8 |

EXAMPLE 4

Determination of Fatty Acid Residues Binding Site in Triacylglycerols

The binding site of the fatty acid residue in the triacylglycerols obtained in Example 3 was analyzed as follows. The triacylglycerols obtained in Example 3 (molecular species: 16:0–16:0–22:6) were dried, and treated with lipase (from *Rhizopus japonicus*) specific for position 1,3. The fatty acid residue was identified using GC/MS after the resulting 2-monoacylglycerols were trimethylsilylated. Lipase treatment was performed in 2 ml of 50 mM acetate buffer (pH 5.5) with 1000 units of lipase at 35° C. for 30 minutes. The reaction products were extracted with ether and trimethylsilylated using commercially available trimethylsilylating agent.

A fragment peak corresponding to the molecular weight of monoacylglycerols to which 22:6 is attached was observed, indicating that the triacylglycerols are 16:0–22:6–16:0 to which fatty acid residues of 22:6 are attached on position 2 of glycerol backbones.

EXAMPLE 5

Preparation of Modified Milk Containing DHA and DPA

Modified milk containing DHA and DPA was prepared by adding 0.44 g of the lipids in Example 1, which contains 46.2% DHA and 10.6% DPA, to 100 g of powdered milk.

The composition of DHA and DPA in the resulting milk were 0.80% and 0.19% of total fatty acids, respectively, which was similar to that of human milk.

EXAMPLE 6

Preparation of Structured Lipids Containing DHA and DPA 50 ml of lipase solution (5,600 U/ml, lipase specific for position 1,3 from *Rhizopus delemar*) was mixed with 2.5 g of $CaCO_3$ as an immobilizing carrier. The enzyme was immobilized and precipitated by adding 40 ml of acetone to the mixture, and the immobilized enzyme was then dried. The specific activity of the resulting immobilized enzyme was 9.3 U/mg. 120 mg of the immobilized enzyme was mixed with 1 g of DHA and DPA-containing lipids obtained from SAM2180 in Example 1, 2 g of caprylic acid, and 60 mg of water with agitation at 30° C. for 8 hours. Triacylglycerols were then recovered from the reaction mixture using a conventional method and the fatty acid composition of the triacylglycerols was determined. The results are shown in Table 6.

TABLE 6

|  | 8:0 | 14:0 | 15:0 | 16:0 | 17:0 | 18:0 | 20:4 (AA) | 20:5 (EPA) | 22:5 (DPA) | 22:6 (DHA) |
| --- | --- | --- | --- | --- | --- | --- | --- | --- | --- | --- |
| No treatment | 0.0 | 2.7 | 2.4 | 55.0 | 1.0 | 1.4 | 0.0 | 0.2 | 6.7 | 28.7 |
| After lipase treatment | 36.2 | 1.8 | 1.2 | 17.6 | 1.0 | 1.8 | 0.0 | 0.2 | 7.3 | 30.4 |

More than 30% triacylglycerols have polyunsaturated fatty acids in the SN2 position of glycerols. So, these lipids are suitable for making structured lipids which contain medium chain fatty acids in the SN1 and SN3 position of glycerols and polyunsaturated fatty acids in the SN2 position of glycerols.

INDUSTRIAL APPLICABILITY

Lipids which contain a high amount of DHA and/or DPA and a low amount of EPA can be obtained by the process of the present invention. DHA and/or DPA may also be obtained by further separating it from the lipids.

The lipids containing DHA and/or DPA, the separated DHA and the separated DPA of the present invention are useful as an additive for foods, feedstuffs, baits, medicament and the like. For feedstuffs or baits, cells containing DHA and/or DPA of the present invention may be used. Poultry egg or poultry egg yolk enriched for DHA and/or DPA may be produced by feeding poultries with the feedstuffs of the present invention.

What is claimed is:

1. A process for preparing lipids containing docosahexaenoic acid and/or docosapentaenoic acid, the process comprising:

providing a culture, the culture comprising a culture medium and the microorganism Ulkenia sp. SAM 2179, FERM BP-5061;

cultivating the microorganism in the culture medium under conditions suitable for the production of lipids containing docosahexaenoic acid and/or docosapentaenoic acid; and recovering said lipids from the culture.

2. A process for preparing docosahexaenoic acid, the process comprising:

cultivating in a nutrient medium the microorganism Ulkenia sp. SAM 2179, FERM BP-5061;

recovering lipids from the medium;

hydrolyzing said lipids to prepare docosahexaenoic acid; and recovering said docosahexaenoic acid.

3. A process for preparing docosapentaenoic acid, the process comprising:

cultivating in a nutrient medium the microorganism Ulkenia sp. SAM 2179, FERM BP-5601;

recovering lipids from the medium;

hydrolyzing said lipids to prepare docosapentaenoic acid; and recovering said docosapentaenoic acid.

4. A process for preparing structured lipids containing docosahexaenoic acid or docosapentaenoic acid, the process comprising:

cultivating in a nutrient medium the microorganism Ulkenia sp. SAM 2179, FERM BP-5061;

culturing the microorganism for a sufficient time to produce lipids containing triacylglycerol having long chain fatty acids at positions 1 to 3 of its glycerol backbone, wherein the long chain fatty acid of at least position 2 comprises docosahexaenoic acid or docosapentaenoic acid;

recovering said lipids from the medium;

treating said lipids with fungal lipase and a source of medium chain fatty acids to convert the long chain fatty acids at positions 1 and 3 of said glycerol backbone of the triacylglycerol into medium chain fatty acids; and recovering said structured lipids.

* * * * *